US006258352B1

(12) United States Patent
Shimonaka

(10) Patent No.: US 6,258,352 B1
(45) Date of Patent: Jul. 10, 2001

(54) COMPOSITIONS AND METHODS OF TREATING THROMBOCYTOPENIA WITH IL-15

(75) Inventor: Yasushi Shimonaka, Gotemba (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 08/930,656

(22) PCT Filed: Apr. 2, 1996

(86) PCT No.: PCT/JP96/00898

§ 371 Date: Dec. 17, 1997

§ 102(e) Date: Dec. 17, 1997

(87) PCT Pub. No.: WO96/31230

PCT Pub. Date: Oct. 10, 1996

(30) Foreign Application Priority Data

Apr. 2, 1995 (JP) .................................................. 7-112218

(51) Int. Cl.[7] .................................................. C07K 1/00
(52) U.S. Cl. .......................................... 424/85.2; 530/351
(58) Field of Search .............................. 424/85.2; 530/351

(56) References Cited

U.S. PATENT DOCUMENTS 5,552,303 * 9/1996 Grabstein et al. .................. 435/69.1
5,747,024 * 5/1998 Grabstein et al. .................. 424/85.2

FOREIGN PATENT DOCUMENTS 96 90 7755    2/1998  (EP) .

OTHER PUBLICATIONS

Sheeran et al, *British J. Anaesthesia*, 78(2) 1997 p 201–219. (Abst Only).*
Atamas et al, *Life Sciences*, 61(12) 1997, p 1105–12 (Abst Only).*
Ishibashi, T. et al., Human Interleukin 6 is a Direct Promoter of Maturation of Megakaryocytes In Vitro, Proc. Natl. Acad. Sci., U.S.A., 86, 5953–5957 (1989).
Ishibashi, T. et al., Interleukin–6 is a Potent Thrombopoietic Factor In Vivo in Mice, Blood, 74, 1241–1244 (1989).
Williams, N. et al., Two–Factor Requirement for Murine Megakaryocyte Colony Formation, J. Cell. Physiol., 110, 101–104 (1982).
Teramura, M. et al., Clonal Growth of Human Megakaryocyte Progenitors in Serum–Free Cultures: Effect of Recombinant Human Interleukin 3, Exp. Hematol., 16, 843–848 (1988).
Teramura, M. et al., Effect of Recombinant Hemopoietic Growth Factors on Human Megakaryocyte Colony Formation in Serum–Free Cultures, Exp. Hematol., 17, 1011–1016 (1989).
Teramura, M. et al., The Effect of Cytokines on the Ploidy of Megakaryocytes, Int. J. Cell Cloning, 8, 245–252 (1990).
Teramura, M. et al., Interleukin–11 Enhances Human Megakaryocytopoiesis In Vitro, Blood, 79, 327–331 (1992).
Bruno, E. et al., Interacting Cytokines Regulate In Vitro Human Megakaryocytopoiesis Blood, 73, 671–677 (1989).
De Sauvage, F.J. et al., Stimulation of Megakaryocytopoiesis and Thrombopoiesis by the c–mpl Ligand, Nature, 369, 533–538 (1994).
Kaushansky, K. et al., Promotion of Megakaryocyte Progenitor Expansion and Differentiation by the C–MPI Ligand Thrombopoietin, Nature, 369, 568–571 (1994).
Grabstein, Kenneth et al., Cloning of a T Cell Growth Factor That Interacts with the β Chain of the Interleukin–2 Receptor, Science, 264, 965–968 (1994).
Nagasawa, T. et al., Maturation of Megakaryocytes Derived from Megakaryocytic Progenitors, Acta Haematologica Japonica, 49, 1688–1695 (1986).
Metcalf, D. et al., Growth of Mouse Megakaryocyte Colonies In Vitro, Proc. Natl. Acad. Sci., U.S.A., 72, 1744–1748 (1975).
Nakeff, Alexander et al., In Vitro Colony Assay for a New Class of Megakaryocyte Precursor: Colony–Forming Unit Megakaryocte, Proc. Soc. Exp. Biol. Med., 151, 587–590 (1976).
Carson, William E. et al., Interleukin (IL) 15 is a Novel Cytokine That Activates Human Natural Killer Cells via Components of the IL–2 Receptor, Journal of Experimental Medicine, vol. 180, No. 4, 1994, pp. 1395–1403.

* cited by examiner

Primary Examiner—Lorraine Spector
Assistant Examiner—Dong Jiang
(74) Attorney, Agent, or Firm—Clark & Elbing LLP

(57) ABSTRACT

It has been revealed that human interleukin-15 (hIL-15) acts on the megakaryocyte-thrombocyte system to accelerate its differentiation, maturation and/or proliferation, thereby accelerating the formation of thrombocytes. The present invention provides a treatment using IL-15 for thrombocytopenia and diseases accompanied by thrombocyte dysfunctions.

1 Claim, 5 Drawing Sheets

COMPOSITIONS AND METHODS OF TREATING THROMBOCYTOPENIA WITH IL-15

FIELD OF THE INVENTION

The present invention relates to a pharmaceutical composition for treating thrombocytopenia which comprises as an active ingredient human interleukin-15 (to be described hereinafter as "hIL-15") having activity to promote the differentiation, maturation and/or proliferation of megakaryocyte-thrombocyte cells and the production of platelets through actions on the cells. Since hIL-15 of this invention acts on the megakaryocyte-thrombocyte system to accelerate the differentiation, maturation and/or proliferation thereof to thereby accelerate the formation of thrombocytes, it is useful especially in the field of medical care as an active ingredient of therapeutic and preventive agents for thrombocytopenia and for thrombocytopenic purpura associated with chemotherapy and bone marrow transplantation and for various diseases characterized by the tendency for bleeding attributable to thrombocytopenia and the like.

BACKGROUND OF THE INVENTION

Blood, which is an indispensable medium for somatic cells constituting the living body, contains blood cells such as erythrocytes, leucocytes, lymphocytes, and thrombocytes. These cells have their own functions and contribute to the maintenance of homeostasis of the living body. It has been a longtime subject of research in the field of hematology to clarify the essential features of differentiation, maturation and proliferation of the blood cells in vivo. It has become recently apparent that the various blood cells are differentiated and maturated from hematopoietic stem cells of the bone marrow and various types of humoral factors in vivo participate in the processes of differentiation and maturation.

From these findings, the humoral factors are expected to be used as a medicament for curing diseases with decreases in blood cells, and the like. Until now there were found various humoral factors including erythropoietin (EPO), G-CSF, GM-CSF, M-CSF, and interleukin (IL) and some of them have been used practically as medical agents which are capable of promoting the differentiation and maturation of blood cells such as erythrocyte, leucocyte, lymphocyte lineages, or the like.

Thrombocytes are akaryocytes with diameters of 2–3 μm present in the blood and one of the tangible components in the blood, which play an important role in arrest of hemorrhage and formation of thrombus in vivo. It has become apparent that megakaryoblasts are formed within the bone marrow from hematopoietic stem cells via progenitor cells to mature to megakaryocytes and the cytoplasm of the megakaryocytes is fragmented to form thrombocytes, which are released into the blood.

Recently various results of researches on megakaryocyte-thrombocyte system have been reported. For example, it has been reported that IL-6 has activity to promote the maturation of megakaryocytes, which is a precursor cell of thrombocyte [Ishibashi T. et al., Proc. Natl. Acad. Sci. USA 86, 5953–5957 (1989), Ishibashi T. et al., Blood 74, 1241–1244 (1989)].

According to the research conducted so far, it is considered that two factors that act differently contribute to the formation of megakaryocyte colonies from bone marrow cells [Williams N. et al., J. Cell. Physiol., 110, 101 (1982)]. The report shows that one is a megakaryocyte colony stimulating factor, Meg-CSF, which forms the megakaryocyte colonies by itself, while the other is a megakaryocyte potentiating factor, Meg-POT, which does not have activity to form megakaryocyte colonies by itself, but has activity to increase the number of megakaryocyte colonies and to promote the maturation of the colonies in the presence of the Meg-CSF.

For example, IL-3 [Teramura M. et al, Exp. Hematol., 16, 843 (1988)] and granulocytes-macrophage colony stimulating factor [Teramura M. et al, Exp. Hematol., 17, 1011 (1989)], and the like were reported as factors having Meg-CSF activity in humans. While IL-6 [Teramura M. and Mizoguthi H., Int. J. Cell Cloning, 8, 245 (1990)], IL-11 [Teramura M. et al, Blood, 79, 327 (1992)] and erythropoietin [Bruno E. et al., Blood, 73, 671 (1989)], and the like were reported as factors having Meg-POT activity in humans.

However, it is known that most of these factors are not the factors that specifically act on megakaryocyte-thrombocyte system but to express their effects through actions on other cells of the blood system or cells not belonging to blood cell system. Thus, there is a risk that not only the expected actions but also other actions would be expressed when these factors are administered as medical agents in anticipation of the actions on the megakaryocyte-thrombocyte system. For example, the above-described IL-6 has various actions other than those mentioned above. From the fact that IL-6 is deeply involved in induction of inflammation as an acute phase reactive protein in vivo, there may be a risk of severe side effects if it is used as a medical agent as it is. Recently c-Mpl ligand has been reported to have both weak Meg-CSF and strong Meg-POT activities [dc Sauvage F. J. et al., Nature, 369, 533 (1994), Kaushansky K. et al., Nature, 369, 568 (1994)]. However, because of paucity of findings on the actions of c-Mpl ligand, practicability of this substance as a medical agent is still unknown.

Thus, as far as factors acting on megakaryocyte-thrombocyte system are concerned, it is important to find out biologically active substances that strongly acts on the megakaryocyte-thrombocyte system and have high activity to promote their differentiation, maturation and/or proliferation. The development of such biologically active has been strongly demanded in the art.

"IL-15 is a protein with a molecular weight of ca 140,00; human IL-15 was purified by Grabstein et al. [*Science*, 264, 965, (1994), hereby incorporated by reference] based on the proteins ability to support the proliferation of a mouse T cell line. Isolation of the gene revealed that a mature protein with 114 amino acid residues was formed by cleavage of a precursor with 162 amino acid residues. The genomic sequence of human IL-15 is given in Krause et al. (1996) *Cytokine* 8(9):667–674, hereby incorporated by reference. Human IL-15 is expressed well in placenta, monocytes of peripheral blood and skeletal muscle, while it is also expressed weakly in heart, lung, liver, and kidney, and the like. As to the biological activities of IL-15, there is a report describing its actions to support differentiation and proliferation of T and B cells, to activate NK cells, and to induce CTL and LAK activities. Accordingly, IL-15 is considered to be a cytokine involved mainly in immunological processes such as proliferation, differentiation, and activation of lymphocytes.

SUMMARY OF THE INVENTION

The present inventors investigated biologically active substances which act on the megakaryocyte-thrombocyte system, to promote the differentiation, maturation and/or proliferation of cells of the megakaryocyte-thrombocyte system and the formation of thrombocytes. IL-15 was found to have such activity.

Accordingly, an object of the present invention is to provide a pharmaceutical composition for treating or preventing (and in some cases, curing) thrombocytopenia, comprising human IL-15 (hIL-15) as an active ingredient.

Another object of the present invention is to provide a pharmaceutical composition comprising hIL-15 as an active ingredient which is effective for treating, curing or preventing diseases derived from thrombocytopenia and diseases accompanied by thrombocyte dysfunctions.

DETAILED DESCRIPTION

Figure 1:
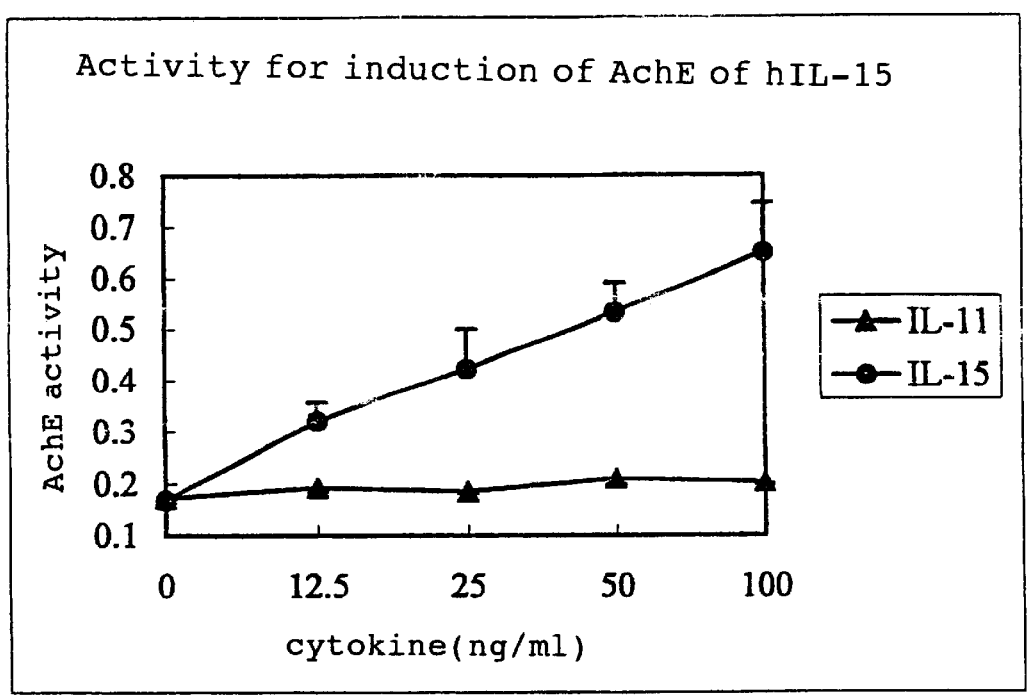
FIG. 1 depicts the induction of AchE activity by hIL-15.

The invention will be described in greater detail below.

In the present invention it was found that hIL-15 has an activity to act on the rodent megakaryocyte-thrombocyte system and promote the production of acetylcholinesterase ("AchE"). Since acetylcholinesterase is an enzyme that is produced in association with differentiation and/or maturation of rodent megakaryocytes [Acta. Haematol. JPN., 49, 1688–1695 (1986)], the activity to promote the production of AchE indicates the action of hIL-15 on the megakaryocyte-thrombocyte system.

In the present invention hIL-15 was found to have activity on the megakaryocyte-thrombocyte system. Activity on megakaryocyte-thrombocyte systems, as used here, means the ability to promote the differentiation and maturation of megakaryocytes or its progenitor cells, or the ability to promote the formation of thrombocytes from megakaryocytes.

To measure the above-mentioned activity of hIL-15 of the present invention on the megakaryocyte-thrombocyte system, bone marrow cells or megakaryocytic cells were incubated with the test substances, followed by detection or measurement of proteins or enzymes specific to megakaryocytes or thrombocytes.

Since rodent megakaryocytes produce AchE accompanied with their differentiation and maturation, the above-mentioned activity of biologically active substances on the megakaryocytes-thrombocytes system can be measured by, for example, counting the number of cells producing AchE by staining the cells or measuring the activity of AchE produced with a spectrophotometer [Toshiro Nagasawa et al., Acta Haematologica Japonica, 49, 1688–1695 (1986)].

As is discussed below, it became apparent from the results of measuring AchE by the above method that hIL-15 of this invention acted on megakaryocytes to promote the production of AchE, and to promote the differentiation and maturation of the megakaryocyte cells to form thrombocytes.

In addition, by conducting a megakaryocytes colony assay [Metcalf D. et al., Proc. Natl. Acad. Sci. U.S.A., 72, 1744 (1975)], it was found that hIL-15 alone showed activity to produce megakaryocytes colonies (Meg-CSF activity).

In the following the pharmaceutical composition for curing thrombocytopenia of the present invention will be described.

The pharmaceutical composition of the present invention comprises hIL-15 as an active ingredient. Recombinant hIL-15 is known in the art and is commercially available, e.g., from Prepro Tech Co., Catalog No. 200-15. hIL-15, with the full length of natural amino acid sequence or an active fragment of the sequence corresponding to the appropriate active site of the molecule can be used. The pharmaceutical composition of the present invention containing hIL-15 which has been subjected only to pharmaceutically necessary processing such as lyophilization, or sterilization by filtration can fully exert its effect. As a matter of course, pharmaceutically acceptable auxiliary components can be added if necessary to make pharmaceutical preparations using ordinary methods. Not only natural hIL-15 but also recombinant hIL-15 can be used for the present invention. Various cells, either procaryotic or eucaryotic, can be used as host cells for the production of recombinant hIL-15. For examples, *Eschericia coli* (for unglycosylated hIL-15) and mammalian cells (for glycosylated protein) can be used.

The auxiliary components include pharmaceutically acceptable bases, stabilizers, antiseptics, preservatives, emulsifiers, suspending agents, solvents, solubilizers, lubricants, correctives, colorants, aromatics, soothing agents, vehicles, binders, thickeners (viscosity increasing agent), and buffers, and the like. Specirid examples thereof inlcude calcium carbonate, lactose, sucrose, sorbitol, mannitol, starch, amylopectin, cellulose derivatives, gelatin, cacao butter, distilled water for injection, sodium chloride solution, Ringer solution, glucose solution, human serum albumin (HSA), and the like.

In order to prepare the pharmaceutical composition of the present invention using the above auxiliary components, suitable components may be selected and used referring to the List of Pharmaceutical Excipients (published by the Medical Regulatory Affairs Committee of the Pharmaceutical Manufacturers' Association of Tokyo and Medical Regulatory Affairs Committee of Osaka Pharmaceutical Manufacturers Association). The amount of auxiliary components may be chosen within a pharmaceutically acceptable range depending on the form of the pharmaceutical composition and the like.

The dose of the pharmaceutical composition of the present invention may be determined depending on the state, age, sex, and body weight of the patients. Dosage generally will fall in the range used for other hematopoietically active therapeutic proteins, e.g., G-CSF (available from Amgen Corporation).

The method of administration may be chosen depending on the state of the patients from various methods of administration such as oral, intramuscular, intraperitoneal, intradermal, subcutaneous, intravenous, intraarterial, or rectal administration. Preferably, the hIL-15 composition is administered by injection.

The therapeutic composition is useful for therapeutic and preventive agents of thrombocytopenia and thrombocytopenic purpura accompanying chemotherapy or bone marrow transplantation, various diseases with hemorrhagic tendency attributable to thrombocytopenia, and patients with malfunction of blood megakaryocytes and/or thrombocytes.

EXAMPLES

In the following examples, the present invention will be described in more detail, but is not to be construed to be limited to these embodiments. Abbreviations commonly used in the art will be used in the following description.

Example 1

Measurement of Acetylcholinesterase Activity (in the Absence of IL-3).

To 100 μl of murine bone marrow cells (C57BL/6N strain, 11–15 weeks of age) diluted to 1×106 cells/ml with "RPMI 1640" (Gibco Co.) supplemented with "1% 'Nutridoma•SR'" (Boehringer Mannheim Co.) (to be called in the following as "culture medium A") was added 50 μl of each of the following three compositions: (1) hIL-15 (Prepro Tech Co./catalog No. 200-15) dissolved in culture medium A to a predetermined concentration, (2)human IL-11 (Pepro Tech Co.) dissolved in culture medium A to a predetermined concentration as negative control, and (3) mouse IL-3 (Boehringer Mannheim Co.) dissolved in culture medium A to a predetermined concentration as positive control. The total amount of each composition was cultured with the bone marrow cells in a 96-well culture place (Corning Co.) at 37° C. and 100% humidity, in 5% $CO_2$/95% air.

On the 6th culture day, 50 μl of a solution containing 0.265 mM DTNB (Sigma Co.), 1% Triton X-100, 1M Tris-HCl (pH 7.2) was added to the culture and its absorbance (referred to as "absorbance A") was measured at 415 nm. Fifty μl of 3 mM acetylthiocholine iodide was further added. After allowing to stand for 30 minutes at room temperature, the absorbance of this solution (referred to as "absorbance B") was measured at 415 nm. The value of "absorbance B"–"absorbance A" was regarded as AchE activity.

Figure 2:
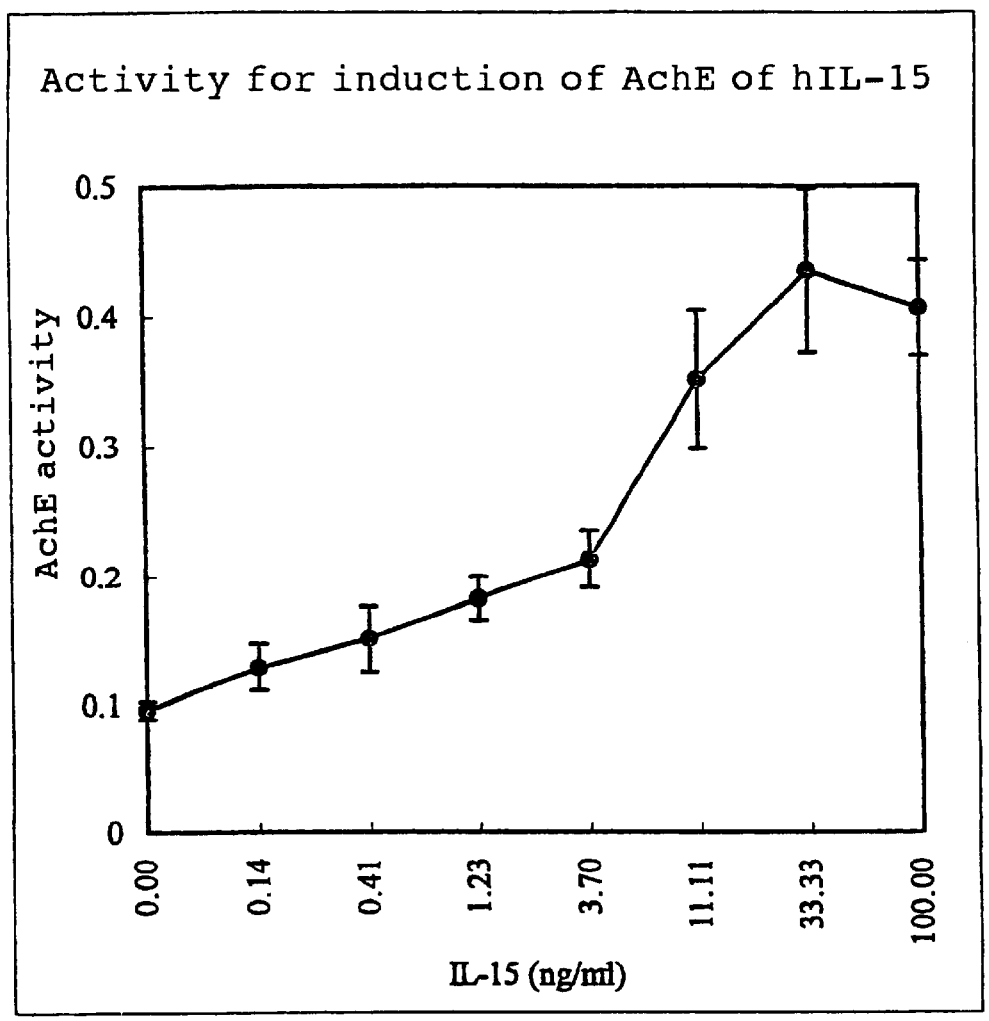
FIG. 2 depicts the induction of AchE activity by hIL-15.
Figure 3:
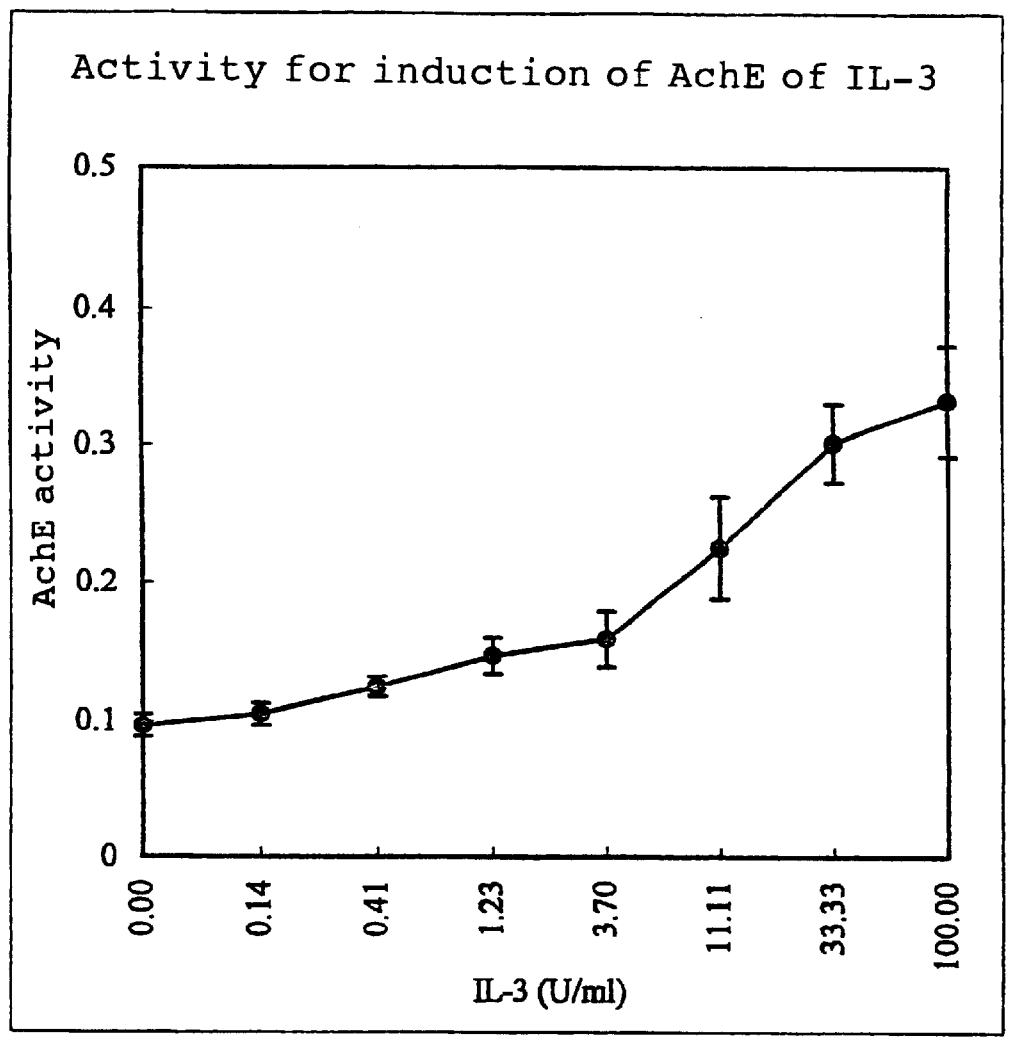
FIG. 3 depicts the induction of AchE activity by IL-3.
Figure 4:
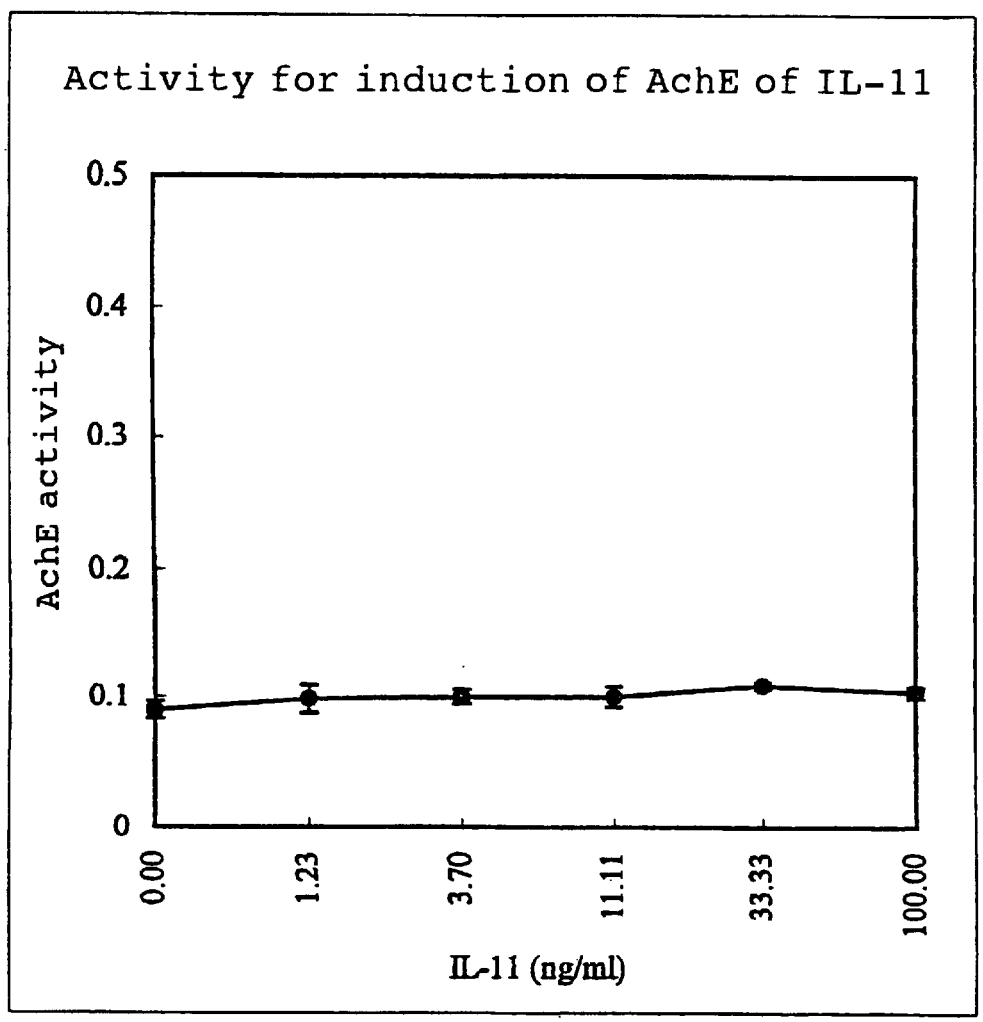
FIG. 4 depicts the induction of AchE activity by IL-11.

FIGS. 1–4 depict the results. The abscissa in each graph shows the concentration of each IL at the time of culturing on the 96-well culture plates, while the ordinate depicts the AchE activity mentioned above ("absorbance B"–"absorbance A"). In FIG. 1 the closed circles represent the data obtained with IL-15 and the closed triangles, those obtained with IL-11 used as a negative control. FIG. 2 depicts the data obtained with hIL-15 with concentrations different from those used in FIG. 1. FIG. 3 depicts the data obtained with IL-11, as a negative control with concentrations different from those used in FIG. 1. FIG. 4 depicts the data obtained with IL-3 alone as a positive control. In the absence of IL-3, IL-15 showed the activity to induce AchE activity equal to or even greater than that of IL-3 in mouse bone marrow cells, which indicates that IL-15 was capable of promoting differentiation and maturation of megakaryocytic cells derived from mouse bone marrow cells.

Example 2
Measurement of Acetylcholinesterase Activity (in the Presence of IL-3).

The experiments were conducted in the same manner as in Example 1 except that recombinant mouse IL-3 (Boehringer Mannheim Co.) was added to a final concentration of 0.75 ng/ml (0.5 ng/ml at the time of culture) to 100 μl of mouse bone marrow cells diluted to 1×106 cells/ml with "RPMI 1640" supplemented with 1% "Nutridoma•SR". As described above, IL-11 is known to exhibit Meg-Pot activity in the presence of IL-3, namely, a Meg CSF. Thus, in contrast to Example 1, IL-11 represents a positive control in this example.

Figure 5:
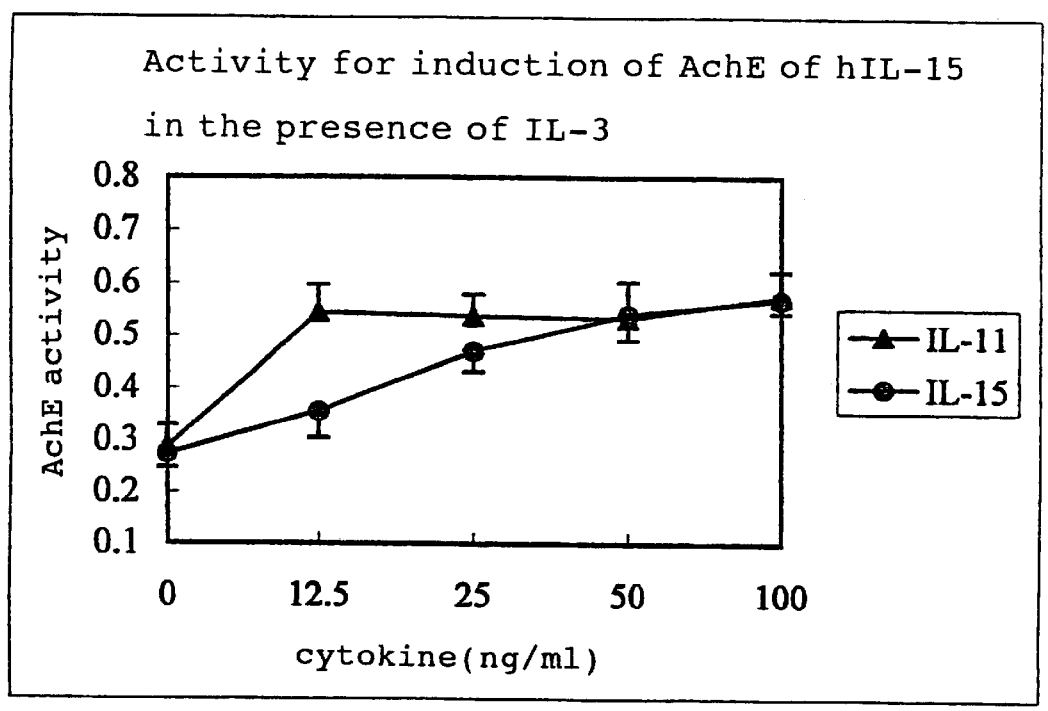
FIG. 5 depicts the induction of AchE activity by IL-15 in the presence of IL-3.

FIG. 5 depicts the results. The abscissa depicts the concentrations of each IL at the time of culturing on the 96-well culture plates, while the ordinate depicts the above-mentioned AchE activity ("absorbance B"–"absorbance A").

In FIG. 5, closed circles represent the data obtained with IL-15, while the closed triangles represent those obtained with IL-11 used as a positive control. IL-15 was found to have activity to induce AchE in mouse bone marrow cells even in the presence of IL-3. Thus, it became apparent that IL-15 had the ability to differentiate and maturate megakaryocytes derived from mouse bone marrow cells even in the absence of IL-3.

Example 3
Megakaryocytes Colony Assay

Using mouse bone marrow cells experiments were conducted with monolayer soft agar culture method. 0.2 ml of horse serum (treated at 56° C. for 30 minutes, Biocell Co.), 0.1 ml (2×106/nuclear cells) of bone marrow cells from the thigh bone of the mouse (C57BL/6N strain male, 6–12 weeks of age), 0.2 ml of "Iscove's Modified Dulbecco's culture medium" (IMDM), 0.4 ml of "Modified McCoy's 5A culture medium" containing 0.75% agar and 0.1 ml of an IL-15 solution [IL-15 (Pepro Tech Co./catalog No. 200-15) was dissolved in IMDM to 100 ng/ml were mixed together, poured into a plastic tissue culture dish of 35 mm diameter and solidified. Culturing was conducted at 37° C. and 100% humidity, in 5% $CO_2$/95% air.

At the 6th culture day whole cultured material removed together with the agar layer was placed on a slide glass and dried to a film-like preparation. The preparation was fixed with 5% glutaraldehyde. AchE staining and counting of the number of megakaryocytes colonies were conducted by the method of Nakeff et al [Proc. Soc. Exp. Biol. Med., 151, 587 (1976)]. Conglomerates containing more than 4 AchE staining positive cells were regarded as a megakaryocyte colony. The magnification of the microscope was set at 200-fold. As a result, thirty megakaryocyte colonies were observed when hIL-15 was added to the culture medium to a final concentration of 10 ng/ml. Only 2 megakaryocyte colonies were found in experiments conducted under the same conditions except for the absence of hIL-15. These findings indicate that hIL-15 alone stimulates proliferation of megakaryocytic cells.

INDUSTRIAL APPLICABILITY

By revealing that hIL-15 acts on the megakaryocyte-thrombocyte system to accelerate its differentiation, maturation and/or proliferation, thereby accelerating the formation of thrombocytes, the present invention provides a pharmaceutical composition comprising hIL-15 as an active ingredient which is effective for treating or preventing diseases resulting in thrombocytopenia and diseases accompanied by thrombocyte dysfunctions.

What is claimed is:

1. A method for treating thrombocytopenia in a human patient, said method comprising administering to said patient a human interleukin-15 in an amount effective for treating thrombocytopenia.

* * * * *